United States Patent [19]

Benedict et al.

[11] Patent Number: 5,028,415

[45] Date of Patent: Jul. 2, 1991

[54] ORAL COMPOSITIONS AND METHOD FOR REDUCING DENTAL CALCULUS

[75] Inventors: James J. Benedict, Norwich, N.Y.; Rodney D. Bush, Cincinnati; Richard J. Sunberg, Oxford, both of Ohio

[73] Assignee: The Procter & Gamble Company, Cincinnati, Ohio

[21] Appl. No.: 285,578

[22] Filed: Dec. 16, 1988

Related U.S. Application Data

[60] Division of Ser. No. 86,212, Aug. 17, 1987, Pat. No. 4,846,650, which is a continuation of Ser. No. 806,156, Dec. 6, 1985, abandoned.

[51] Int. Cl.$^5$ .......................... A61K 7/24; A61K 9/68; A61K 7/16; A61K 7/18
[52] U.S. Cl. ......................................... 424/55; 424/49; 424/52; 424/48; 424/464; 514/900; 514/901; 514/902; 514/835
[58] Field of Search ....................... 424/49, 52, 48, 55, 424/464; 514/900-902, 835

[56] References Cited

U.S. PATENT DOCUMENTS

| | | | |
|---|---|---|---|
| 3,429,963 | 2/1969 | Shedlovsky | 424/56 |
| 3,776,850 | 12/1973 | Pearson | 252/89 |
| 4,304,766 | 12/1981 | Chang | 424/52 |
| 4,627,977 | 12/1986 | Gaffar | 424/52 |
| 4,654,159 | 3/1987 | Bush | 252/95 |
| 4,661,341 | 4/1987 | Benedict | 424/48 |
| 4,846,650 | 7/1989 | Benedict | 424/55 |

FOREIGN PATENT DOCUMENTS

| | | |
|---|---|---|
| 2408591 | 9/1975 | Fed. Rep. of Germany . |
| 72/898 | 9/1972 | South Africa . |

OTHER PUBLICATIONS

Matsuzawa, *Chemical Abstracts*, vol. 82 (1975), 170648c.

Primary Examiner—F. T. Moezie
Attorney, Agent, or Firm—Milton B. Graff, IV; Kim W. Zerby; Jack D. Schaeffer

[57] ABSTRACT

The present invention relates to oral compositions, such as dentifrices, toothpastes and mouthwashes, which provide an anticalculus benefit. These compositions comprise a safe and effective amount of an anticalculus agent which is a polyepoxysuccinic acid, or its pharmaceutically-acceptable salts, along with a pharmaceutically-acceptable carrier. The present invention also relates to a method for inhibiting or reducing the development of dental calculus by contacting the oral cavity with a safe and effective amount of an anticalculus agent which is a polyepoxysuccinic acid, or its pharmaceutically-acceptable salt.

12 Claims, No Drawings

ORAL COMPOSITIONS AND METHOD FOR REDUCING DENTAL CALCULUS

This is a division of application Ser. No. 086,212, filed on Aug. 17, 1987, now U.S. Pat. No. 4,846,650 issued July 11, 1989, which is a continuation of application Ser. No. 806,156, filed Dec. 6, 1985, now abandoned.

BACKGROUND OF THE INVENTION

The present invention relates to oral compositions, such as dentifrices, toothpastes and mouthwashes, which provide an anticalculus benefit. The present invention further relates to methods for inhibiting or reducing calculus.

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are regarded by many as a constant source of mechanical irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The literature discloses a number of chelating agents for this purpose. British Patent 490,384, Feb. 15, 1937, discloses oral compositions containing ethylenediaminetetraacetic acid, nitrilotriacetic acid and related compounds as anticalculus agents. U.S. Pat. No. 3,737,533, June 5, 1973 to Francis discloses oral compositions containing certain carbonyl diphosphonates. U.S. Pat. No. 3,678,154, July 18, 1972 to Widder et al. discloses oral compositions containing certain polyphosphonates and fluoride.

Organic polymeric agents have also been taught for use as anticalculus agents. For example, U.S. Pat. No. 3,429,963, Feb. 25, 1969 to Shedlovsky discloses copolymers of maleic anhydride and ethylene, and polyacrylic acid having an average molecular weight of 1500 and greater. Another example is Dyroff et al; U.S. Pat. No. 4,289,753; Issued Sept. 15, 1981 which discloses that oral compositions containing certain bis(carboxyalkoxy)butanedioic acid compounds inhibit dental calculus formation. Also, U.S. Pat. No. 4,138,477, Feb. 6, 1979 to Gaffar discloses compositions effective in preventing calculus containing as the essential agent a zinc-polymer combination, with the anionic polymer containing carboxylic, sulfonic and/or phosphonic acid groups. In spite of the many known types of anticalculus agents, the need for improved anticalculus products still exists.

Accordingly, it is an object of the present invention to provide oral compositions comprising certain types of polycarboxylic acids, or their pharmaceutically-acceptable salts, and a pharmaceutical carrier, which compositions can deliver an effective anticalculus benefit. It is a further object of the present invention to provide such an anticalculus product in the form of compositions which do not inhibit remineralization of the teeth, and which are cosmetically acceptable. It is a further object of the present invention to provide an effective method for treating calculus utilizing the polycarboxylic acid-based compositions of the present invention.

SUMMARY OF THE INVENTION

The present invention relates to oral compositions, such as toothpastes, toothpowders, mouthwashes, chewing gums, mouth sprays, lozenges and sachets. Such compositions comprise:
(a) a safe and effective amount of an anticalculus agent which is a polyepoxysuccinic acid, or its pharmaceutically-acceptable salts; and
(b) a pharmaceutically-acceptable carrier.

The present invention also relates to a method for inhibiting or reducing the development of dental calculus comprising contacting the oral cavity (e.g., by brushing or rinsing or masticating) with a safe and effective amount of an anticalculus agent which is a polyepoxysuccinic acid, or its pharmaceutically-acceptable salt.

DETAILED DESCRIPTION OF THE INVENTION

The compositions of the present invention comprise a safe and effective amount of polyepoxysuccinic acid, or its pharmaceutically-acceptable salts, and a pharmaceutically-acceptable carrier. The compositions preferably may be in the form of various oral products, such as toothpastes, toothpowders, mouthwashes, chewing gums, mouth sprays, lozenges, or sachets. The form of the product depends on the pharmaceutically-acceptable carrier which is used.

The anti-calculus agent useful in the compositions of the present invention is polyepoxysuccinic acid, or its pharmaceutically-acceptable salts. Generally, such polyepoxysuccinic acid polymers have the formula:

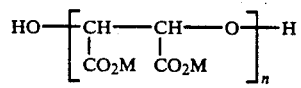

wherein n indicates the number of monomeric units which make up the polyepoxysuccinic acid chain, with n being an integer of 2 or larger; and wherein the M's are hydrogens, pharmaceutically-acceptable cations, or mixtures thereof. For convenience, this polyepoxysuccinate material, whether in its free acid or salt form, can be designated as "PESA".

Generally the compositions and methods of the present invention will utilize polyepoxysuccinic acid oligomers, or their pharmaceutically-acceptable salts, having n values in the range of from about 2 to about 1000, with from about 2 to about 50 preferred, from about 2 to about 25 more preferred, and from about 4 to about 10 most preferred. For use in the present invention, polyepoxysuccinic acids or salts of the foregoing type may, of course, be combined with unpolymerized succinic acid (i.e., tartaric acid and/or epoxysuccinate) or other similar materials not of the type hereinbefore described. This is, of course, acceptable so long as the compositions and methods herein utilize at least an effective amount of particular polyepoxysuccinic acid or salt oligomers which do fall within the foregoing definition.

Because the polyepoxysuccinic acids, or their pharmaceutically-acceptable salts, are generally synthesized as a mixture of various chain-length polyepoxysuccinic acid polymers, it is generally not economically desirable or necessary for the purposes of the present invention to use a single particular chain-length polyepoxysuccinic acid (e.g., all polymers having n=8). Therefore, the polyepoxysuccinic acid, or pharmaceutically-acceptable salts, utilized in the present invention will generally be mixtures of various chain length polymers. The average molecular weight of such polymer mixtures can be determined using a carbon-13 nuclear magnetic resonance ($C_{13}NMR$) technique, described in greater detail hereinafter in the Preparation Examples. In general, $C_{13}NMR$ measures the ratio of carbon atoms which are attached to hydroxy moieties ("hydroxy carbons") relative to the carbon atoms which are attached to ether oxygens ("ether carbons"). As the molecular weight of the polyepoxysuccinic acid increases (i.e., longer chain length oligomers), the ratio of hydroxy carbons to ether carbons decreases. This ratio can be determined and used to calculate an average molecular weight value.

Useful polymer mixtures of polyepoxysuccinic acid will generally have an average molecular weight (determined by $C_{13}NMR$) for the acid of at least about 200, preferably above about 400, with an average molecular weight of at least about 500 more preferred, and at least about 650 most preferred. Preferred ranges for the average molecular weight of the polyepoxysuccinic acid mixtures are from about 200 to about 500,000, with from about 200 to about 20,000 preferred, from about 400 to about 10,000 more preferred, and from about 500 to about 5000 most preferred. A particularly preferred polyepoxysuccinic acid material has an average molecular weight of about 650.

If the pharmaceutically-acceptable salts of the polyepoxysuccinic acid are utilized, the above average molecular weight ranges should be adjusted (by taking into consideration the mass of the cation of the salt relative to the mass of the proton of the acid) such that the range for the salt corresponds to the range of the acid form of the salt being utilized. For example, the sodium salt of the particularly preferred polyepoxysuccinic acid mixture has an average molecular weight of about 900 (i.e., adjusted from the acid form's average molecular weight of about 650).

For purposes of this invention, the terms "pharmaceutically-acceptable salts" and "pharmaceutically-acceptable cation", as used herein, mean salts, or cations which form salts, of polyepoxysuccinic acid which are effective as anti-calculus agents, and which are acceptable from a toxicity viewpoint. Non-limiting examples of preferred pharmaceutically-acceptable salts and cations for PESA include alkali metal (e.g., sodium, potassium), and unsubstituted or substituted ammonium (preferably substituted with low molecular weight alkyl groups; e.g., trimethylammonium; tetramethylammonium).

Synthesis of polyepoxysuccinic acid can be carried out by those skilled in the art using methods disclosed in, for example, West German Patent 2,408,591, to Henkel and Cie, GmbH, published Sept. 4, 1975, and in U.S. Pat. No. 3,776,850, to Pearson et al., issued Dec. 4, 1973, both patents being incorporated herein by reference.

In the processes of U.S. Pat. No. 3,776,850, polyepoxysuccinic acid is prepared by the polymerization of the diethyl ester of 1-oxacyclopropane-2,3-dicarboxylic acid followed by subsequent saponification (e.g., with aqueous NaOH) of the resulting polymer. The literature generally describes various methods for effecting this polymerization. (See *Polymerization of Aldehydes and Oxides*, J. Furakawa, T. Saegusa, Interscience Publishers, New York, Chapter 3, pages 125-204 (1963); and *Preparative Methods of Polymer Chemistry*, Second Edition, W. R. Sorenson, T. W. Campbell, Interscience Publishers, New York, Chapter 5, Subchapter VI, pages 367-382.

For example, one process which may be used for the production of polyepoxysuccinic acid comprises refluxing the diethyl ester of 1-oxacyclopropane-cis-2,3-dicarboxylic acid in the presence of toluene and a catalyst such as $BF_3$ at a temperature of about 115° C. and at atmospheric pressure. The diethyl ester which is polymerized may be obtained by the esterification of 1-oxacyclopropane-cis-2,3-dicarboxylic acid with triethylorthoformate, as described in *Chemistry and Industry* (London), H. Cohen, J. D. Mier, page 349 (1965). The 1-oxacyclopropane-cis-2,3-dicarboxylic acid which is esterified can be prepared from maleic acid by the method disclosed in *Journal of Organic Chemistry*, G. B. Payne, P. H. Williams, Vol. 24, page 54 (1959).

Another process of preparing the polyepoxysuccinic acid, or its pharmaceutically-acceptable salts, comprises reacting a soluble epoxysuccinate with a molar equivalent quantity of calcium hydroxide in aqueous media, esterifying the resultant product, separating the ester from the reaction mixture, and saponifying the ester to the salt. A more practical process for preparing the polyepoxysuccinic acid, or its pharmaceutically-acceptable salts, involves alkaline hydrolysis of maleic anhydride to a maleate salt, catalytic oxidization to an epoxysuccinate and then treatment with at least about 5%, preferably from about 10% to about 80%, of a molar equivalent amount of calcium hydroxide to form a mixture of alkali metal and calcium salts of the polyepoxysuccinic acid.

The essential feature of these synthesis processes is the use of calcium hydroxide or other alkaline calcium salts in the oligomerization of epoxysuccinates or in the telomerization of epoxysuccinates with tartrates or other hydroxyacids or salts thereof. The use of calcium as described hereinbelow promotes a high yield of the polyepoxysuccinic acid, or its pharmaceutically-acceptable salts, when compared with, for example, the boron trifluoride catalyst used in the process disclosed in the U.S. Pat. No. 3,776,850, to Pearson et al., incorporated by reference hereinabove.

Synthesis of polyepoxysuccinic acid-based anticalculus agents useful in the present invention is illustrated by the following Preparation Examples.

PREPARATION EXAMPLE I

PESA is prepared by carrying out the following reactions in a manner described in detail hereinafter.

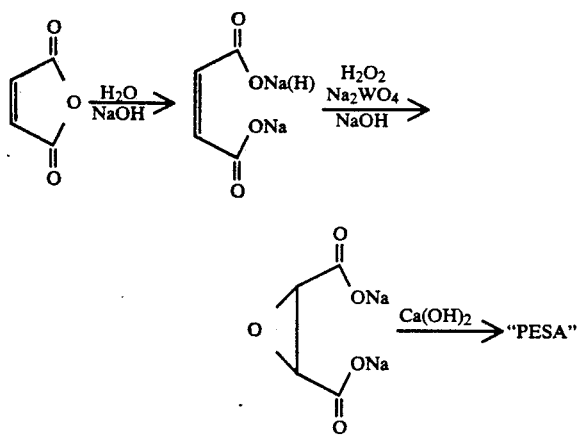

(A) Synthesis of Epoxysuccinate Disodium Salt 4.0 mole of maleic anhydride is dissolved in 1.2 liters of deionized water. This solution is placed in a 5 liter 3-necked flask equipped with an addition funnel charged with 8 moles of 50% aqueous sodium hydroxide and another addition funnel charged with 4.8 moles of 30% aqueous hydrogen peroxide. The reaction flask is also equipped with a pH probe and a mechanical stirrer. To the flask containing the maleic anhydride solution is added 6.0 moles of sodium hydroxide to give a pH of approximately 5.7 and a reaction temperature is maintained at approximately 70° C.

Addition of sodium hydroxide is followed by the addition of 0.08 moles of sodium tungstate dihydrate and a greenish-yellow color is noted. While maintaining the temperature between about 60°-65° C. and the pH between about 5-5.6, approximately 2 moles of sodium hydroxide and 4.8 moles of hydrogen peroxide are added to the reaction mixture. An ice bath is necessary at times during this ½ hour addition period. After the addition is completed, the solution is maintained at 70° C. with a heating mantle for 1.5 hours. The reaction solution is then allowed to cool to room temperature and enough sodium hydroxide is added to give a pH of 10. After transferring the solution to a 5-gallon container, 8 liters of acetone is slowly added to precipitate the product epoxysuccinate disodium salt. This product is collected on filter paper and allowed to dry.

(B) Formation of Polyepoxysuccinic Acid Sodium Salt 1.7 moles of epoxysuccinate disodium salt prepared as set forth in part A hereinbefore is added into a 1-liter flask equipped with a mechanical stirrer and an oil bath. 16.6 moles of deionized water is added to the flask and the resulting mixture is stirred for 15 minutes followed by the addition of 0.17 moles of calcium hydroxide. The reaction flask containing this mixture is placed in the oil bath heated to 100° C. for 2 hours. The resulting slightly yellow reaction solution is allowed to cool to room temperature and then mixed with 2 liters of deionized water. The pH of this solution is reduced to 2.8 using an acid ion exchange resin (Dowex 50W-X8, acid form). The acid resin is removed by filtration and the filtrate concentrated by evaporation under reduced pressure to give a thick viscous oil. Methanol (0.5 liters) is added to this oil and the resulting precipitate is collected, and then washed with 0.1 liter of methanol. This solid is dissolved in 1 liter of deionized water and the pH is adjusted to 9.5 with sodium hydroxide. The solution is evaporated and dried at 100° C. under vacuum for 24 hours to give the polyepoxysuccinate sodium salt as a white powder.

High pressure liquid chromatography (HPLC) analysis indicates the following distribution of oligomers for the PESA material of this Preparation Example I: n=1 (5.1%); n=2 (2.8%); n=3 (3.9%); n=4 (5.5%); n=5 (8.3%); n=6 (8.0%). The remainder is higher molecular weight oligomers.

An average molecular weight for the PESA polymer mixture of Preparation Example I is determined using $C_{13}$NMR analysis. The $C_{13}$NMR spectra used for such average molecular weight determinations are obtained by using a carbon 13 nuclear magnetic resonance spectrometer (e.g., Varian CFT-20; Bruker FX-270; Joel FX-90Q). The $C_{13}$NMR spectra are obtained in standard fashion except that: (1) the pulse delay and related parameters are set to 5 seconds so that each carbon atom has ample time to relax between pulses, so that the resulting area corresponding to each carbon atom is proportional to the number of each type of carbon atom present; and (2) the $C_{13}$NMR spectra is integrated. As a check to verify whether the integrations are accurate, the carbonyl carbons are integrated vs. the total ether and hydroxyl carbons and evaluated to assure the expected ratio.

The relationship between the amounts of ether and hydroxy carbon atoms present in the polymer mixture and the average molecular weight of the mixture can be calculated from the relationship:

$$\bar{n}(1-A/B)=1$$

wherein $\bar{n}$ is the average number of monomeric units in the chain length of the average length PESA oligomer; A is the integrated area of the ether carbons from the $C_{13}$NMR spectrum; and B is the total integrated area of the combined ether and hydroxy carbons from the $C_{13}$NMR spectrum. For example, if A=7.2 $C_{13}$NMR integration units and B=9.1 $C_{13}$NMR integration units, then $\bar{n}$=4.78 (i.e., the average length of the oligomers in the mixture is 4.78 monomeric units long). The average molecular weight is therefore 860 (i.e., 4.78×the molecular weight of the monomeric unit in the oligomers as its sodium salt form plus 18, which is the molecular weight of the H and OH which complete the oligomeric formula; or (4.78×176)+18=860). Using this $C_{13}$NMR technique, the average molecular weight for the PESA of this Preparation Example I is determined to be about 900 (based on molecular weight of sodium salt form).

PREPARATION EXAMPLE II

Maleic anhydride (22.3 g, 0.227 mol, F.W. 98) is dissolved in 32 ml of water and while this solution is cooled in an icebath, 29.3 g (50% soln., 0.34 mol) of sodium hydroxide solution is added. The resulting solution is placed in a 500 ml roundbottom flask which is equipped with a magnetic stirring bar, pH probe, thermometer and an addition funnel. This reaction flask is then placed in an oil bath at 60° C. and when the reaction solution reaches 55° C., 27 g of 30% hydrogen peroxide (0.238 mol) and 0.784 g (0.0024 mol) of sodium tungstate is added and the pH of the reaction solution maintained at 5-7 by addition of 9.1 g (50% solution, 0.224 mol) of sodium hydroxide. After about 40 minutes, an exotherm is noted (50° to 100° C.). The solution is allowed to cool to 60° C. and maintained at this temperature for an additional hour. Then 0.84 g (0.0114 mol) of calcium hydroxide is added to the reaction solution followed by heating to 100° C. for 2 hrs. A sample of the reaction solution indicates that a substantial amount of epoxysuccinate remains. 0.84 g (0.0114 mol) additional calcium hydroxide is added and the reaction heated to 100° C. for an additional 2 hours. The volatiles are then removed by vacuum, and the resulting solid dried under vacuum at 100° C. for 16 hrs to give 43.4 g of white solid which comprises a mixture of sodium and calcium salts of 2,6-dihydroxy-3,5-dicarboxy-4-oxa-1,7-heptanedioic acid (approx. 5%), higher molecular weight oligomers of epoxysuccinic acid, and tartaric acid (approx. 20%).

PREPARATION EXAMPLE III

Disodium epoxysuccinate (prepared as in Preparation Example I), disodium d,l-tartrate, calcium hydroxide and water are mixed in a molar ratio of 0.75:0.25:0.5:16. The mixture is maintained at 80° C. for 30 minutes.

The resultant product on a dry basis contains 70% oligomers of epoxysuccinic acid salts and 25% tartaric acid salts. Calcium is removed by acidification to pH 2 and use of an acid ion exchange poly (sulfonated styrene) resin. The oligomers are precipitated by addition of methanol at pH 2.5. Most of the tartaric acid remains soluble. The polyepoxysuccinic acid oligomer is then converted to a sodium salt with NaOH.

The distribution of oligomers on a weight basis is determined to be approximately:

$n=2(51\%)$; $n=3(21\%)$; $n=4(21\%)$; and $n>4(13\%)$

The average molecular weight (sodium salt form) of this composition is approximately 450.

A reduction in calcium hydroxide level from a 0.5 molar ratio level to a 0.1 molar level results in the following approximate distribution:

$n=2(22\%)$; $n=3(21\%)$; $n=4(21\%)$; and $n>4(35\%)$.

The average molecular weight (sodium salt form) of this composition is approximately 700.

PREPARATION EXAMPLE IV

Disodium epoxysuccinate (prepared as in Preparation Example I), calcium hydroxide and water are mixed in a molar ratio of 1.0:0.1:16. The mixture is maintained at 80° C. for 30 minutes.

The resultant product on a dry basis contains 93% oligomers of polyepoxysuccinic acid and 7% tartaric acid salts. The calcium and tartaric acid content of the mixture can be reduced as described in Preparation Example III, or by the precipitation of calcium ions with sodium carbonate, sodium silicate or similar materials.

The distribution of oligomers on a weight basis is determined to be approximately:

$n=2(8\%)$; $n=3(10\%)$; $n=4(13\%)$; $n>4(69\%)$

The average molecular weight (sodium salt form) of this composition is approximately 1000.

An increase in calcium hydroxide level from a 0.1 molar ratio level to a 0.25 molar level results in the following approximate distribution:

$n=2(20\%)$; $n=3-4 (35\%)$; $n=3$ to $6(70\%)$; $n>6(10\%)$

The average molecular weight (sodium salt form) of this composition is approximately 700.

As noted, the oral compositions of the present invention comprise a safe and effective amount of the polyepoxysuccinates as hereinbefore described in combination with a pharmaceutically-acceptable carrier. The term "pharmaceutically-acceptable carrier", as used herein, means any suitable vehicle which is non-toxic, which is not unacceptably reactive with the polyepoxysuccinic acid anticalculus agent, and which can be used to deliver or apply the present compositions to the oral cavity. Such carriers include the usual components of mouthwashes, toothpastes, tooth powders, prophylaxis pastes, lozenges, chewing gums, mouth sprays, sachets, and the like and are more fully described hereinafter. Dentifrices (including toothpastes, gels and toothpowders) and mouthwashes are the preferred systems.

In general, the pharmaceutically-acceptable carrier can comprise from about 0.1% to about 99.9% by weight of the oral compositions herein, preferably from about 50% to about 99.9%, with from about 80% to about 99% most preferred. Depending on what type of oral composition is desired, the safe and effective amount of the polyepoxysuccinate anticalculus agent can comprise from about 0.1% to about 99.9% by weight of the compositions, preferably from about 0.1% to about 50%, with from about 1% to about 20% most preferred. Particular kinds of such compositions are illustrated as follows. All percentages and ratios used hereinafter are by weight unless specified otherwise.

Dentifrice compositions (e.g., toothpastes, toothgels, and toothpowders) generally comprise in addition to the polyepoxysuccinic acid, or its pharmaceutically-acceptable salts, a pharmaceutically-acceptable carrier which can comprise the usual and conventional components of these dentifrice compositions. For example, the dentifrices of the present invention may include abrasive polishing material, flavoring agents, sweetening agents, coloring agents, emulsifying agents, water-soluble fluorides, thickening agents, humectants, alcohols, and/or water. A safe and effective amount of the polyepoxysuccinic acid, or its pharmaceutically-acceptable salts, in dentifrice compositions of the present invention can range from about 0.1% to about 50%, with from about 1% to about 20% more preferred, and from about 1% to about 10% most preferred.

The abrasive polishing material contemplated for use in the dentifrice compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 to about 30 microns, preferably between about 5 and about 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the trade name "Syloid" by the W. R. Grace & Company, Davison Chemical Division. Preferred precipitated silica materials include those marketed by the J. M. Huber Corporation under the trade name, "Zeodent", particularly the silica carrying the designation "Zeodent 119". These silica abrasives are described in U.S. Pat. No. 4,340,583, July 29, 1982, incorporated herein by reference.

The abrasive in the dentifrice compositions described herein is generally present at a level of from about 6% to about 70%, preferably from about 15% to about 25% when the dentifrice is a toothpaste. Higher levels, as high as 90%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977, incorporated herein by reference.

It is common to have a water-soluble fluoride compound present in dentfrices in an amount sufficient to give a fluoride concentration of from about 0.0025% to about 5.0% by weight, preferably from about 0.005% to about 2.0% by weight, to provide additional anticaries effectiveness. Preferred fluorides are sodium fluoride, stannous fluoride, indium fluoride, and sodium monofluorophosphate. Norris et al., U.S. Pat. No. 2,946,735, issued July 26, 1960 and Widder et al., U.S. Pat. No. 3,678,154, issued July 18, 1972 disclose such salts as well as others.

Water is also usually present in the toothpastes of this invention. Water employed in the preparation of commercially suitable toothpastes should preferably be de-ionized and free of organic impurities. Water generally comprises from about 10% to about 50%, preferably from about 20% to about 40%, by weight of the toothpaste compositions herein. These amounts of water include the free water which is added plus that which is introduced with other materials such as with humectants, e.g., sorbitol.

In preparing toothpastes, it is generally necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from about 0.5% to about 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can comprise the pharmaceutically-acceptable carrier for the present invention. Mouthwashes generally comprise a water/ethyl alcohol solution (water:ethyl alcohol ratio from about 20:1 to about 2:1) and preferably other ingredients such as flavor, sweeteners, humectants and sudsing agents such as those mentioned above for dentifrices. The humectants, such as glycerin and sorbitol give a moist feel to the mouth. Generally, on a weight basis, the mouthwashes of the invention comprise: about 5% to about 60% (preferably about 10% to about 25%) ethyl alcohol; about 0% to about 20% (preferably about 5% to about 20%) of a humectant; about 0% to about 2% (preferably about 0.01% to about 0.15%) emulsifying agent; about 0% to about 0.5% (preferably about 0.005% to about 0.06%) sweetening agent such as saccharin; about 0% to about 0.3% (preferably about 0.03% to about 0.3%) flavoring agent; and the balance water. The amount of polyepoxysuccinic acid, or its pharmaceutically-acceptable salts, in mouthwashes is from about 0.1% to about 20%, typically from about 1% to about 10%.

Other embodiments of the oral compositions herein include lozenges and chewing gums. Suitable lozenge and chewing gum components are disclosed in U.S. Pat. No. 4,083,955, Apr. 11, 1978 to Grabenstetter et al., incorporated herein by reference.

The pH of the present compositions and/or the pH of such compositions in the mouth can be any pH which is safe for the hard and soft tissues of the oral cavity. Such pH values generally range from about 3 to about 10, preferably from about 4 to about 8.

The compositions of the present invention can be made using methods which are common in the oral products field. For example, toothpaste compositions may be prepared by mixing part of the humectant and water together and heating to 66°–71° C. The fluoride source, if present, is then added along with the sweetener, the polyepoxysuccinic acid and/or its pharmaceutically-acceptable salt, the opacifier and the flavor. To this mixture is added the abrasive which is mixed in well. The thickener is then slurried with the remainder of the humectant and milled prior to being added to the other components.

The present invention further relates to a method for reducing or inhibiting the development of dental calculus by contacting the oral cavity, especially the teeth or dentures, with a safe and effective amount of a polyepoxysuccinic acid, or its pharmaceutically-acceptable salts. The phrase "safe and effective amount", as used herein, means an amount of polyepoxysuccinic acid, or its pharmaceutically-acceptable salts, which is sufficient to reduce or inhibit dental calculus while being safe to the hard and soft tissues of the oral cavity. Generally, an amount of at least about 0.01 grams, preferably at least about 0.025 grams, of the polyepoxysuccinic acid, or its pharmaceutically-acceptable salts, in the oral cavity is effective. Generally, the amount used is within from about 0.01 grams to about 5 grams, with from about 0.025 grams to about 1.0 grams preferred, and from about 0.05 grams to about 0.5 grams most preferred. The preferred method for contacting the oral cavity for the method of treatment of the present invention involves brushing the teeth or dentures with a toothpaste composition of the present invention.

The following examples further describe and demonstrate preferred embodiments of compositions and methods of use within the scope of the present invention. The examples are given solely for illustration and are not to be construed as limitations of this invention, since many variations of the present invention are possible without departing from the spirit and scope thereof.

EXAMPLE I

The following composition is representative of a dentifrice composition of the present invention.

| Component | Weight % |
| --- | --- |
| Sorbitol (70% aqueous solution) | 35.000 |
| Water | 29.351 |
| PEG-6[1] | 1.000 |
| Silica Dental Abrasive[2] | 20.000 |
| Sodium Fluoride | 0.243 |
| Titanium dioxide | 0.500 |
| Sodium saccharin | 0.286 |
| Sodium alkyl sulfate (27.9% aqueous solution) | 4.000 |
| Flavor | 1.040 |
| Carboxyvinyl Polymer[3] | 0.300 |
| Carrageenan[4] | 0.800 |
| Polyepoxysuccinic acid[5] | 7.480 |
| | 100.000 |

[1] PEG-6 = Polyethylene glycol having molecular weight of 600.
[2] Precipitated silica identified as Zeodent 119 offered by J. M. Huber.
[3] Carbopol offered by B. F. Goodrich Company.
[4] Iota Carrageenan offered by Hercules Chemical Company.
[5] Polyepoxysuccinic acid mixture in its sodium salt form having an average molecular weight of about 900 prepared by the method of Preparation Example I.

EXAMPLE II

This composition is another example of a dentifrice of the present invention.

| Component | Weight % |
| --- | --- |
| Sorbitol (as in Example I) | 35.000 |
| Water | 29.653 |
| Sodium Fluoride | 0.243 |
| PEG-6 (as in Example I) | 1.000 |
| Carrageenan (as in Example I) | 0.800 |
| Sodium saccharin | 0.280 |
| Titanium dioxide | 0.500 |
| Flavor | 1.044 |
| Silica Dental Abrasive (as in Example I) | 20.000 |
| Sodium alkyl sulfate (as in Example I) | 4.000 |
| Polyepoxysuccinic acid (as in Example I) | 7.480 |
| | 100.000 |

The compositions of Example I and II are effective anticalculus products, and are cosmetically acceptable.

In the above compositions the abrasive may be replaced by equivalent amounts of other abrasives such as calcium carbonate, calcium pyrophosphate, tricalcium phosphate, dicalcium othophosphate dihydrate and hydrated alumina with similar results being obtained. Similarly, other thickeners, such as gum arabic and carboxymethyl cellulose may be used as well as other fluoride sources such as stannous fluoride, potassium fluoride, indium fluoride, zinc fluoride and sodium monofluorophosphate. Silicas are the preferred abrasives when fluoride sources are used in the compositions. Other polyepoxysuccinic acid polymers having mass average molecular weights above about 500 may also be used in equivalent amounts in place of the 1000 molecular weight material. Daily use of 1 gram of the compositions in Examples I or II to brush the user's teeth or dentures results in inhibition and reduction of the development of dental calculus.

EXAMPLE III

The following mouthwash composition is another composition of the present invention.

| Component | Weight % |
| --- | --- |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | 76.48 |
| Polyepoxysuccinic acid (as in Example I) | 5.00 |
| | 100.00 |

EXAMPLE IV

The following is a lozenge composition of the present invention.

| Component | Weight % |
| --- | --- |
| Sorbitol | 17.5 |
| Mannitol | 17.5 |
| Starch | 13.6 |
| Sweetener | 1.2 |
| Flavor | 11.7 |
| Color | 0.1 |
| Polyepoxysuccinic acid (as in Example I) | 4.4 |
| Corn syrup | balance |

EXAMPLE V

The following is a chewing gum composition of the present invention.

| Component | Weight % |
| --- | --- |
| Sorbitol crystals | 38.44 |
| Paloja-T gum base [1] | 20.00 |
| Sorbitol (70% Aqueous solution) | 22.00 |
| Mannitol | 10.00 |
| Glycerin | 7.56 |
| Flavor | 1.00 |
| Polyepoxysuccinic acid (as in Example I) | 1.00 |
| | 100.00 |

[1] Supplied by L. A. Dreyfus Company

The compositions of Examples III, IV and V are also effective anticalculus products and are cosmetically acceptable. Daily use of a composition of Examples III, IV, or V by contacting with the oral cavity of the user results in inhibition and reduction of the development of dental calculus.

What is claimed is:

1. An oral composition effective for reducing the development of dental calculus, which composition comprises:
   (a) from about 0.1% to about 50% of an anticalculus agent which is a polyepoxysuccinic acid, or a pharmaceutically-acceptable salt thereof, having the formula

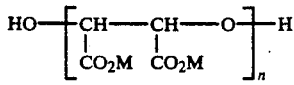

wherein M is hydrogen or a pharmaceutically-acceptable cation, and n is an integer of from about 2 to about 25; and (b) from about 50% to about 99.9% of a pharmaceutically-acceptable carrier comprising a flavoring agent or a sweetening agent;

said composition being in the form of a dentifrice (toothpaste, tooth gel, tooth powder), mouthwash, mouth spray, lozenge, chewing gum or sachet.

2. An oral composition according to claim 1 wherein, in the formula for said polyepoxysuccinic acid, or its pharmaceutically-acceptable salt, n is an integer of from about 4 to about 10.

3. An oral composition according to claim 2 wherein the polyepoxysuccinic acid, or its pharmaceutically-acceptable salt, has an average molecular weight of about 650.

4. An oral composition according to claim 1 which is in the form of a lozenge or chewing gum.

5. An oral composition according to claim 1 which is in the form of a mouthwash, and wherein the pharmaceutically-acceptable carrier comprises one or more mouthwash components selected from ethyl alcohol, water, or mixtures thereof.

6. A mouthwash composition according to claim 5 wherein:

(a) the anticalculus agent comprises from about 0.1% to about 20% by weight of the composition;

(b) the pharmaceutically-acceptable carrier comprises from about 80% to about 99.9% by weight of the composition, and contains one or more additionaly mouthwash components selected from flavorants, sweeteners, humectants, sudsing agents, or mixtures of these components.

7. A dentifrice composition effective for reducing the development of dental calculus, which composition comprises:

(a) from about 0.1% to about 50% of an anticalculus agent which is a polyepoxysuccinic acid, or a pharmaceutically-acceptable salt thereof, having the formula:

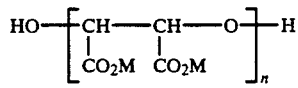

wherein M is hydrogen or a pharmaceutically-acceptable cation, and n is an integer of from about 2 to about 25; and (b) from about 50% to about 99.9% of a pharmaceutically-acceptable carrier which comprises a dental abrasive polishing material.

8. A dentifrice composition according to claim 7 wherein the formula for said polyepoxysuccinic acid, or pharmaceutically-acceptable salt thereof, n is an integer of from about 4 to about 10.

9. A dentifrice composition according to claim 7 wherein (a) the anticalculus agent comprises from about 1% to about 20% by weight of the composition; and (b) the pharmaceutically-acceptable carrier comprises from about 80% to about 99% by weight of the composition.

10. A dentifrice according to claim 9 wherein the pharmaceutically-acceptable carrier, in addition to the dental abrasive, contains one or more additional dentifrice components selected from flavoring agents, sweetening agents, thickening agents, coloring agents, emulsifying agents, humectants, water-soluble fluorides, alcohol, water or mixtures of these components.

11. A dentifrice composition according to claim 10 wherein the dental abrasive polishing material comprises precipitated silica or silica gel.

12. A dentifrice composition according to claim 10 wherein the composition comprises a water-soluble fluoride compound selected from sodium fluoride, stannous fluoride, indium fluoride, sodium monofluorophosphate, or mixtures thereof.

* * * * *

UNITED STATES PATENT AND TRADEMARK OFFICE
CERTIFICATE OF CORRECTION

PATENT NO. : 5,028,415

DATED : July 2, 1991

INVENTOR(S) : J.J. Benedict, R.D. Bush and R.J. Sunberg

It is certified that error appears in the above-identified patent and that said Letters Patent is hereby corrected as shown below:

On the title page item [54] and in column 1:

Title - "METHOD" should be --METHODS--.

Column 13, lines 10-11, "pharmaceutically" should be --orally--.

Column 13, line 13, "said composition being in the form of a dentifrice" should be --wherein said carrier is a dentifrice--.

Column 13, line 14, delete "(toothpaste, tooth gel, tooth powder)".

Column 13, lines 26-28, "which is in the form of a mouthwash and wherein the pharmaceutically-acceptable carrier comprises one or more" should be --wherein the orally acceptable carrier is a mouthwash and contains--.

Column 13, line 35, "pharmaceutically" should be --orally--.

Column 13, line 37, delete "one or more".

Column 13, lines 37-38, "additionaly" should be --additional--.

Column 13, lines 38-39, "flavorants, sweeteners, humectants, sudsing agents" should be --a flavorant, sweetener, humectant, sudsing agent--.

Column 14, line 12, "cation" should be --salt thereof--.

Column 14, lines 14-15, "pharmaceutically" should be --orally--.

Column 14, line 25, "pharmaceutically" should be --orally--.

Column 14, lines 29-30, delete "pharmaceutically-acceptable" and ",in addition to the dental abrasive,".

UNITED STATES PATENT AND TRADEMARK OFFICE
CERTIFICATE OF CORRECTION

PATENT NO. : 5,028,415

DATED : July 2, 1991

INVENTOR(S) : J.J. Benedict, R.D. Bush and R.J. Sunberg

It is certified that error appears in the above-identified patent and that said Letters Patent is hereby corrected as shown below:

Column 14, lines 31-33, "flavoring agents, sweetening agents, thickening agents, coloring agents, emulsifying agents, humectants, water-soluble fluorides" should be --a flavoring agent, sweetening agent, thickening agent, coloring agent, emulsifying agent, humectant, water-soluble fluoride--.

Column 14, line 34, delete "or mixtures of these components".

Signed and Sealed this

Twenty-second Day of December, 1992

*Attest:*

DOUGLAS B. COMER

*Attesting Officer*         *Acting Commissioner of Patents and Trademarks*